US010932857B2

(12) United States Patent
Nikonovas

(10) Patent No.: US 10,932,857 B2
(45) Date of Patent: Mar. 2, 2021

(54) ORTHOPEDIC FIXATION WITH IMAGERY ANALYSIS

(71) Applicant: DePuy Synthes Products, Inc., Raynham, MA (US)

(72) Inventor: Arkadijus Nikonovas, Littleover (GB)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/111,775

(22) Filed: Aug. 24, 2018

(65) Prior Publication Data
US 2019/0000552 A1 Jan. 3, 2019

Related U.S. Application Data

(60) Continuation of application No. 15/461,969, filed on Mar. 17, 2017, now abandoned, which is a division of (Continued)

(30) Foreign Application Priority Data

May 19, 2010 (GB) .................................... 1008281

(51) Int. Cl.
A61B 17/66 (2006.01)
A61B 34/10 (2016.01)
(Continued)

(52) U.S. Cl.
CPC .............. A61B 34/10 (2016.02); A61B 17/62 (2013.01); A61B 17/66 (2013.01); G06F 19/00 (2013.01);
(Continued)

(58) Field of Classification Search
CPC . A61B 17/56; A61B 17/60–663; A61B 34/10; G06T 7/0012–0016; G06T 2207/30008; G06T 2207/30052
See application file for complete search history.

(56) References Cited

U.S. PATENT DOCUMENTS 2,055,024 A 9/1936 Bittner, Jr.
2,391,537 A 12/1945 Anderson
(Continued)

FOREIGN PATENT DOCUMENTS

CN 1494397 5/2004
CN 101296664 A 10/2008
(Continued)

OTHER PUBLICATIONS

Viceconti et al., "A software simulation of tibial fracture reduction with external fixator", Computer Methods and Programs in Biomedicine, 1993, 40, 89-94.
(Continued)

Primary Examiner — Eduardo C Robert
Assistant Examiner — Steven J Cotroneo
(74) Attorney, Agent, or Firm — BakerHostetler

(57) ABSTRACT

Methods of orthopedic fixation and imagery analysis are provided. Images of first and second bone segments attached to a fixation apparatus are captured. Fixator elements identified in the images can be used to obtain imaging scene parameters. Bone elements identified in the images can be used with the imaging scene parameters to reconstruct a three dimensional representation of positions and/or orientations of the first and second bone segments with respect to the fixation apparatus.

20 Claims, 3 Drawing Sheets

Related U.S. Application Data application No. 13/111,180, filed on May 19, 2011, now Pat. No. 9,642,649.

(51) Int. Cl.
*A61B 17/62* (2006.01)
*G16H 30/40* (2018.01)
*G16H 20/40* (2018.01)
*G06F 19/00* (2018.01)
*A61B 90/00* (2016.01)
*A61B 90/14* (2016.01)

(52) U.S. Cl.
CPC .............. *G16H 20/40* (2018.01); *G16H 30/40* (2018.01); *A61B 90/14* (2016.02); *A61B 2090/367* (2016.02); *A61B 2090/3966* (2016.02)

(56) References Cited

U.S. PATENT DOCUMENTS

| | | | |
|---|---|---|---|
| 3,977,397 A | 8/1976 | Kalnberz et al. | |
| 4,081,686 A | 3/1978 | Nieuweboer | |
| 4,450,834 A | 5/1984 | Fischer | |
| 4,489,111 A | 12/1984 | Woodrum | |
| 4,615,338 A | 10/1986 | Ilizarov et al. | |
| 4,620,533 A | 11/1986 | Mears | |
| 4,630,203 A * | 12/1986 | Szirtes | A61B 6/00 356/2 |
| 4,768,524 A | 9/1988 | Hardy | |
| 4,784,125 A | 11/1988 | Monticelli et al. | |
| 4,875,165 A | 10/1989 | Fencil et al. | |
| 4,889,111 A | 12/1989 | Ben-Dov | |
| 4,890,631 A | 1/1990 | Hardy | |
| 4,930,961 A | 6/1990 | Weis | |
| 4,964,320 A | 10/1990 | Lee, Jr. | |
| 4,973,331 A | 11/1990 | Pursley et al. | |
| 5,062,844 A | 11/1991 | Jamison et al. | |
| 5,074,866 A | 12/1991 | Sherman et al. | |
| 5,087,258 A | 2/1992 | Schewior | |
| 5,095,919 A | 3/1992 | Monticelli et al. | |
| 5,108,393 A | 4/1992 | Ruffa | |
| 5,156,605 A | 10/1992 | Pursley et al. | |
| 5,179,525 A | 1/1993 | Griffis et al. | |
| 5,180,380 A | 1/1993 | Pursley et al. | |
| 5,209,750 A | 5/1993 | Stef | |
| 5,275,598 A | 1/1994 | Cook | |
| 5,358,504 A | 10/1994 | Paley et al. | |
| 5,437,668 A | 8/1995 | Aronson et al. | |
| 5,443,464 A | 8/1995 | Russell et al. | |
| 5,451,225 A | 9/1995 | Ross et al. | |
| 5,458,599 A | 10/1995 | Adobbati | |
| 5,540,686 A | 7/1996 | Zippel et al. | |
| 5,601,551 A | 2/1997 | Taylor et al. | |
| 5,630,814 A | 5/1997 | Ross et al. | |
| 5,653,707 A | 8/1997 | Taylor et al. | |
| 5,681,309 A | 10/1997 | Ross et al. | |
| 5,702,389 A | 12/1997 | Taylor et al. | |
| 5,728,095 A | 3/1998 | Taylor et al. | |
| 5,746,741 A | 5/1998 | Kraus et al. | |
| 5,766,173 A | 6/1998 | Ross et al. | |
| 5,776,132 A | 7/1998 | Blyakher | |
| 5,871,018 A | 2/1999 | Delp et al. | |
| 5,885,282 A | 3/1999 | Szabo | |
| 5,891,143 A | 4/1999 | Taylor et al. | |
| 5,919,192 A | 7/1999 | Shouts | |
| 5,951,556 A | 9/1999 | Faccioli et al. | |
| 5,961,515 A | 10/1999 | Taylor et al. | |
| 5,963,612 A | 10/1999 | Navab | |
| 5,967,777 A * | 10/1999 | Klein | A61C 1/084 433/75 |
| 5,968,043 A | 10/1999 | Ross et al. | |
| 5,971,984 A | 10/1999 | Taylor et al. | |
| 5,976,142 A | 11/1999 | Chin | |
| 6,017,341 A | 1/2000 | Windhagen et al. | |
| 6,021,579 A | 2/2000 | Schimmels et al. | |
| 6,030,386 A | 2/2000 | Taylor et al. | |
| 6,047,080 A | 4/2000 | Chen et al. | |
| 6,129,727 A | 10/2000 | Austin et al. | |
| 6,206,566 B1 | 3/2001 | Schuetz | |
| 6,293,947 B1 | 9/2001 | Buchbinder | |
| 6,320,928 B1 | 11/2001 | Vaillant et al. | |
| 6,363,169 B1 | 3/2002 | Ritter et al. | |
| 6,434,278 B1 | 8/2002 | Hashimoto | |
| 6,501,848 B1 | 12/2002 | Carroll et al. | |
| 6,510,241 B1 | 1/2003 | Vaillant et al. | |
| 6,537,275 B2 | 3/2003 | Venturini et al. | |
| 6,701,174 B1 * | 3/2004 | Krause | A61B 17/025 378/21 |
| 6,912,293 B1 | 6/2005 | Korobkin | |
| 7,113,623 B2 | 9/2006 | Chen et al. | |
| 7,187,792 B2 * | 3/2007 | Fu | A61N 5/1049 382/128 |
| 7,226,449 B2 | 6/2007 | Venturini et al. | |
| 7,280,687 B2 | 10/2007 | Ban et al. | |
| 7,306,601 B2 | 12/2007 | McGrath et al. | |
| 7,388,972 B2 | 6/2008 | Kitson | |
| 7,490,085 B2 | 2/2009 | Walker et al. | |
| RE40,914 E | 9/2009 | Taylor et al. | |
| 7,645,279 B1 | 1/2010 | Haupt | |
| 7,657,079 B2 | 2/2010 | Lake et al. | |
| 7,677,078 B2 | 3/2010 | Sauer et al. | |
| 7,758,582 B2 | 7/2010 | Ferrante et al. | |
| 7,828,801 B2 | 11/2010 | Mirza et al. | |
| 7,837,621 B2 | 11/2010 | Krause et al. | |
| 7,887,537 B2 | 2/2011 | Ferrante et al. | |
| 7,955,334 B2 | 6/2011 | Steiner et al. | |
| 8,029,505 B2 | 10/2011 | Hearn et al. | |
| 8,057,474 B2 | 11/2011 | Knuchel et al. | |
| 8,062,293 B2 | 11/2011 | Steiner et al. | |
| 8,147,491 B2 | 4/2012 | Lavi | |
| 8,157,800 B2 | 4/2012 | Vvedensky et al. | |
| 8,202,273 B2 | 6/2012 | Karidis | |
| 8,257,353 B2 | 9/2012 | Wong | |
| 8,282,652 B2 | 10/2012 | Mackenzi et al. | |
| 8,296,094 B2 | 10/2012 | Harrison et al. | |
| 8,323,282 B2 | 12/2012 | Taylor | |
| 8,333,766 B2 | 12/2012 | Edelhauser et al. | |
| 8,377,060 B2 | 2/2013 | Vasta et al. | |
| 8,419,732 B2 | 4/2013 | Mullaney | |
| 8,425,512 B2 | 4/2013 | Vasta et al. | |
| 8,430,878 B2 | 4/2013 | Vasta et al. | |
| 8,439,914 B2 | 5/2013 | Ross et al. | |
| 8,444,644 B2 | 5/2013 | Ross et al. | |
| 8,454,604 B2 | 6/2013 | Wong | |
| 8,469,958 B2 | 6/2013 | Stevens | |
| 8,574,232 B1 | 11/2013 | Ross et al. | |
| 8,654,150 B2 | 2/2014 | Haskell | |
| 8,777,946 B2 | 7/2014 | Lindahl et al. | |
| 8,834,467 B2 | 9/2014 | Singh et al. | |
| 8,858,555 B2 | 10/2014 | Crozet et al. | |
| 8,864,763 B2 | 10/2014 | Murray et al. | |
| 8,906,021 B1 | 12/2014 | Lehmann et al. | |
| 8,945,128 B2 | 2/2015 | Singh et al. | |
| 8,951,252 B2 | 2/2015 | Steiner et al. | |
| 8,952,986 B2 | 2/2015 | Haskell | |
| 9,011,438 B2 | 4/2015 | Steiner et al. | |
| 9,017,339 B2 | 4/2015 | Edelhauser et al. | |
| 9,039,706 B2 | 5/2015 | Murray et al. | |
| 9,044,271 B2 | 6/2015 | Edelhauser et al. | |
| 9,066,756 B2 | 6/2015 | Wong | |
| 9,078,700 B2 | 7/2015 | Ross et al. | |
| 9,101,398 B2 | 8/2015 | Singh et al. | |
| 9,155,559 B2 | 10/2015 | Ross et al. | |
| 9,204,937 B2 | 12/2015 | Edelhauser et al. | |
| 9,220,533 B2 | 12/2015 | Singh et al. | |
| 9,642,649 B2 | 5/2017 | Nikonovas | |
| 9,895,167 B2 | 2/2018 | Edelhauser et al. | |
| 2001/0018617 A1 * | 8/2001 | Copf | A61F 2/36 623/23.26 |
| 2002/0010465 A1 | 1/2002 | Koo et al. | |
| 2003/0106230 A1 | 6/2003 | Hennessey | |
| 2003/0191466 A1 | 10/2003 | Austin et al. | |
| 2004/0039259 A1 | 2/2004 | Krause et al. | |

(56) References Cited

U.S. PATENT DOCUMENTS

| | | |
|---|---|---|
| 2004/0068187 A1 | 4/2004 | Krause et al. |
| 2004/0073211 A1 | 4/2004 | Austin et al. |
| 2004/0073212 A1 | 4/2004 | Kim |
| 2004/0082849 A1* | 4/2004 | Schweikard .......... G06T 19/003 600/424 |
| 2004/0097922 A1 | 5/2004 | Mullaney |
| 2004/0111024 A1 | 6/2004 | Zheng et al. |
| 2004/0133199 A1 | 7/2004 | Coati et al. |
| 2004/0167518 A1 | 8/2004 | Estrada |
| 2004/0208279 A1 | 10/2004 | Xiao et al. |
| 2005/0149018 A1 | 7/2005 | Cooper et al. |
| 2005/0215997 A1 | 9/2005 | Austin et al. |
| 2005/0256389 A1* | 11/2005 | Koga ...................... A61F 2/461 600/407 |
| 2006/0276786 A1 | 12/2006 | Brinker |
| 2007/0043354 A1* | 2/2007 | Koo .................. A61B 17/6416 606/58 |
| 2007/0043429 A1* | 2/2007 | Hegel ....................... A61F 2/82 623/1.15 |
| 2007/0049930 A1 | 3/2007 | Hearn et al. |
| 2007/0161983 A1 | 7/2007 | Cresina et al. |
| 2007/0161984 A1 | 7/2007 | Cresina et al. |
| 2007/0238069 A1* | 10/2007 | Lovald ............... A61B 17/8085 433/173 |
| 2008/0012850 A1 | 1/2008 | Keating, III |
| 2008/0051779 A1 | 2/2008 | Mackenzie et al. |
| 2008/0114267 A1* | 5/2008 | Lloyd ..................... A61B 34/20 600/587 |
| 2008/0234554 A1 | 9/2008 | Vvedensky et al. |
| 2008/0269741 A1 | 10/2008 | Karidis |
| 2009/0036890 A1 | 2/2009 | Karidis |
| 2009/0036892 A1 | 2/2009 | Karidis et al. |
| 2009/0105621 A1 | 4/2009 | Boyd et al. |
| 2009/0143788 A1* | 6/2009 | Fang ....................... A61B 34/20 606/130 |
| 2009/0161945 A1 | 6/2009 | Morgan-Mar et al. |
| 2009/0177198 A1 | 7/2009 | Theodoros et al. |
| 2009/0198234 A1 | 8/2009 | Knuchel et al. |
| 2009/0226055 A1 | 9/2009 | Dankowicz et al. |
| 2009/0275944 A1 | 11/2009 | Huebner et al. |
| 2009/0326532 A1 | 12/2009 | Schulze |
| 2009/0326560 A1* | 12/2009 | Lampropoulos .. A61M 25/0009 606/148 |
| 2010/0030219 A1 | 2/2010 | Lerner et al. |
| 2010/0039421 A1 | 2/2010 | Toyomura et al. |
| 2010/0087819 A1 | 4/2010 | Mullaney |
| 2010/0104150 A1 | 4/2010 | Saint et al. |
| 2010/0172567 A1 | 7/2010 | Prokoski |
| 2010/0179548 A1 | 7/2010 | Marin |
| 2010/0191239 A1 | 7/2010 | Sakkers et al. |
| 2010/0191500 A1 | 7/2010 | Harrison et al. |
| 2010/0234844 A1 | 9/2010 | Edelhauser et al. |
| 2010/0280516 A1 | 11/2010 | Taylor |
| 2010/0305568 A1 | 12/2010 | Ross et al. |
| 2010/0312243 A1 | 12/2010 | Ross et al. |
| 2011/0004199 A1 | 1/2011 | Ross et al. |
| 2011/0029093 A1* | 2/2011 | Bojarski ................. A61F 2/389 623/20.35 |
| 2011/0103676 A1 | 5/2011 | Mullaney |
| 2011/0118737 A1 | 5/2011 | Vasta et al. |
| 2011/0118738 A1 | 5/2011 | Vasta et al. |
| 2011/0131418 A1 | 6/2011 | Teng et al. |
| 2011/0208187 A1 | 8/2011 | Wong |
| 2011/0313418 A1 | 12/2011 | Nikonovas |
| 2011/0313419 A1 | 12/2011 | Mullaney |
| 2012/0041439 A1 | 2/2012 | Singh et al. |
| 2012/0078251 A1 | 3/2012 | Benenati et al. |
| 2012/0232554 A1 | 9/2012 | Shaevitz et al. |
| 2012/0259343 A1 | 10/2012 | Clark et al. |
| 2012/0303028 A1 | 11/2012 | Wong |
| 2012/0330312 A1 | 12/2012 | Burgherr et al. |
| 2013/0041288 A1 | 2/2013 | Taylor et al. |
| 2013/0060146 A1* | 3/2013 | Yang ....................... A61B 6/032 600/476 |
| 2013/0131675 A1 | 5/2013 | Vasta et al. |
| 2013/0138017 A1 | 5/2013 | Jundt et al. |
| 2013/0201212 A1 | 8/2013 | Haskell |
| 2013/0245625 A1 | 9/2013 | Vasta et al. |
| 2013/0289575 A1 | 10/2013 | Edelhauser et al. |
| 2013/0296857 A1 | 11/2013 | Barnett et al. |
| 2014/0135764 A1 | 5/2014 | Ross et al. |
| 2014/0236152 A1 | 8/2014 | Walberg et al. |
| 2014/0257286 A1 | 9/2014 | Lindahl et al. |
| 2014/0276817 A1 | 9/2014 | Murray et al. |
| 2014/0276821 A1 | 9/2014 | Murray et al. |
| 2014/0278325 A1 | 9/2014 | Burgherr et al. |
| 2014/0303670 A1 | 10/2014 | Colloca |
| 2014/0379038 A1 | 12/2014 | Dogramadzi et al. |
| 2015/0080892 A1 | 3/2015 | Lehmann et al. |
| 2015/0088135 A1 | 3/2015 | Singh |
| 2015/0112339 A1 | 4/2015 | Lindahl et al. |
| 2015/0223842 A1 | 8/2015 | Murray et al. |
| 2015/0238227 A1 | 8/2015 | Singh et al. |
| 2015/0257788 A1 | 9/2015 | Jay et al. |
| 2015/0265313 A1 | 9/2015 | Wong |
| 2015/0272624 A1 | 10/2015 | Singh |
| 2015/0305776 A1 | 10/2015 | Ross et al. |
| 2015/0305777 A1 | 10/2015 | Singh et al. |
| 2015/0313641 A1 | 11/2015 | Ross et al. |
| 2016/0022314 A1 | 1/2016 | Bordeaux et al. |
| 2016/0045225 A1 | 2/2016 | Edelhauser et al. |
| 2016/0092651 A1 | 3/2016 | Austin et al. |
| 2016/0113681 A1 | 4/2016 | Singh |
| 2016/0125603 A1 | 5/2016 | Tanji |
| 2017/0181800 A1 | 6/2017 | Nikonovas |
| 2017/0303966 A1 | 10/2017 | Edelhauser et al. |
| 2017/0348054 A1 | 12/2017 | Kumar et al. |
| 2017/0348057 A1 | 12/2017 | Kumar et al. |
| 2017/0354439 A1 | 12/2017 | Mannanal et al. |
| 2018/0055569 A1 | 3/2018 | Wahl et al. |

FOREIGN PATENT DOCUMENTS

| | | |
|---|---|---|
| EP | 1100048 A1 | 5/2001 |
| EP | 1690506 A1 | 8/2006 |
| EP | 2767252 A1 | 8/2014 |
| FR | 2576774 A1 | 8/1986 |
| FR | 2756025 A1 | 5/1998 |
| JP | 2001-523985 A | 11/2001 |
| JP | 2003-144454 A | 5/2003 |
| JP | 2003-530177 A | 10/2003 |
| JP | 2004-254899 A | 9/2004 |
| JP | 2006-507056 A | 3/2006 |
| JP | 2006-218298 A | 8/2006 |
| JP | 2009-505736 A | 2/2009 |
| JP | 2011-512883 A | 4/2011 |
| KR | 20-0443058 Y1 | 1/2009 |
| RU | 2159091 C2 | 11/2000 |
| RU | 2352283 C2 | 4/2009 |
| WO | 98/12975 A2 | 4/1998 |
| WO | 99/59100 A1 | 11/1999 |
| WO | 01/15611 A1 | 3/2001 |
| WO | 01/78015 A2 | 10/2001 |
| WO | 03/30759 A2 | 4/2003 |
| WO | 2007/024904 A2 | 3/2007 |
| WO | 2009/102904 A1 | 8/2009 |
| WO | 2010/002587 A1 | 1/2010 |
| WO | 2010/104567 A1 | 9/2010 |
| WO | 2011/026475 A1 | 3/2011 |
| WO | 2011/060264 A1 | 5/2011 |
| WO | 2011/060266 A1 | 5/2011 |
| WO | 2011/146703 A1 | 11/2011 |
| WO | 2014/186453 A2 | 11/2014 |

OTHER PUBLICATIONS

U.S. Appl. No. 15/247,333, Restriction Requirement dated Apr. 5, 2018, 6 pages.

U.S. Appl. No. 15/461,969, filed Mar. 17, 2017, entitled Orthopedic Fixation with Imagery Analysis, Non-final Rejection dated Feb. 13, 2018.

(56) References Cited

OTHER PUBLICATIONS

U.S. Appl. No. 13/111,180, filed May 19, 2011, entitled Orthopedic Fixation with Imagery Analysis, Notice of Allowance dated Sep. 17, 2014.
U.S. Appl. No. 13/111,180, filed May 19, 2011, entitled Orthopedic Fixation with Imagery Analysis, Notice of Allowance dated Dec. 16, 2016.
U.S. Appl. No. 13/111,180, filed May 19, 2011, entitled Orthopedic Fixation with Imagery Analysis, Notice of Allowance dated Aug. 26, 2016.
U.S. Appl. No. 13/111,180, filed May 19, 2011, entitled Orthopedic Fixation with Imagery Analysis, Notice of Allowability dated Nov. 17, 2016.
U.S. Appl. No. 13/111,180, filed May 19, 2011, entitled Orthopedic Fixation with Imagery Analysis, Non-final Rejection dated Jun. 6, 2013.
U.S. Appl. No. 13/111,180, filed May 19, 2011, entitled Orthopedic Fixation with Imagery Analysis, Non-final Rejection dated Apr. 9, 2015.
U.S. Appl. No. 13/111,180, filed May 19, 2011, entitled Orthopedic Fixation with Imagery Analysis, Final Rejection dated Oct. 23, 2015.
U.S. Appl. No. 13/111,180, filed May 19, 2011, entitled Orthopedic Fixation with Imagery Analysis, Final Rejection dated Feb. 14, 2014.
U.S. Appl. No. 15/247,333, filed Aug. 25, 2016, Non-final Rejection dated Sep. 19, 2018, 21 pages.
Tsai, "A Versatile Camera Calibration Technique for High-Accuracy 3D Machine Vision Metrology Using of-the-shelf TV Cameras and Lenses", IEEE Journal of Robotics & Automation, RA-3, No. 4, Aug. 1987, 323-344.
Trucco et al., "Introductory Techniques of 3-D Computer Vision", 1998, pp. 178-194.
T.A. Larionova et al. "X-ray absorptiometry in the analysis of bone mineral density of a patient with an orthopaedic trauma", Genius of Orthopaedy No. 3, pp. 98-102 (w/English abstract).
Styker, Hoffmann LRF Hexapod, Operative technique, Jul. 2016, 44 pages.
Stryker, Hoffman LRF, Gradual Correction, Operative technique, 2016, 36 pages.
Stoughton et al., "A Modified Stewart Platform Manipulator with Improved Dexterity", IEEE Transactions on Robotics and Automation, Apr. 1993, vol. 9, No. 2, 166-173.
Solomin, The Basic Principles of External Fixation Using the Ilizarov Device, 2005, 371 pages.
Solomin et al., Deformity Correction and Fracture Treatment by software-based Ortho-SUV Frame, User Manual, For SUV-Software vp 2.1, Vreden Russian Research Institute of Traumatology and Orthopedics, (Ortho-SUV) Ltd., Saint Petersburg, 2016, 158 pages.
Solomin et al., Deformity Correction and Fracture Treatment by software-based Ortho-SUV Frame, User Manual, For SUV-Software vp 1.0 and vr 1.0, Vreden Russian Research Institute of Traumatology and Orthopedics, (Ortho-SUV) Ltd., Saint Petersburg, 2013, 144 pages.
Solomin et al., Deformity Correction and Fracture Treatment by software-based Ortho-SUV Frame User Manual Draft, year and date of publication are unknown, 90 pages.
Simard et al., "The Ilizarov Procedure: Limb Lengthening and Its Implications", Physical Therapy, Jan. 1992, vol. 72, No. 1, 25-35.
Russakoff et al., "Intensity-Based 2D-3D Spine Image Registration Incorporating a Single Fiducial Marker", Academic Radiology, Jan. 2005, vol. 12, No. 1, 37-50.
Ren L, Feng Z, Mills JK. A self-tuning iterative calculation approach for the forward kinematics of a Stewart-Gough platform. In Mechatronics and Automation, Proceedings of the 2006 IEEE International Conference on Jun. 25, 2006, 2018-2023.
Parikh PJ, Lam SS. A hybrid strategy to solve the forward kinematics problem in parallel manipulators. IEEE Transactions on Robotics. Feb. 2005; 21(1): 18-25.

Paley, "The principles of deformity correction by the Ilizarov technique: Technical aspects", Techniques in Orthopaedics, 1989, vol. 4, Issue 1, 15-29.
Paley et al., "Deformity Correction by the Ilizarov Technique", Operative Orthopaedics, 1993, 883-948.
Orthofix, TL-HEX Software User's Guide: Software version 1.4, Nov. 2015, 60 pages.
Ortho-SUV Frame—Art of Deformity Correction, Ortho-SUV Ltd, captured by https://web.archive.org from http://www.miito.org/download/ortho-suv-frame-eng.pdfon Jun. 13, 2010; 11 pages.
Nikonovas, Arkadijus. Taylor Spatial Frame: Kinematics, Mechanical Properties and Automation. Diss. University of Bristol, May 2005, 230 pages.
Maiocchi etl.; "Instruments and Their Use"; Operative Principles of Ilizarov; Chapter 2, 1991, 26 pages.
Maiocchi et al., "Operative Principles of Ilizarov", Chapter 2, 1991, 26 pages.
Kelly, "Flow to calculate 3D coordinates with two cameras, a calibration object, a java program, and a lot of MS Excel macros", Jun. 10, 2002, 9 pages.
Hartley, "Euclidian Reconstruction from Uncalibrated Views", Applications of Invariance in Computer Vision, 1994, vol. 825, pp. 237-256.
Garreau et al., "A Knowledge-Based Approach for 3-D Reconstruction and Labeling of Vascular Networks from Biplane Angiographic Projections", IEEE Transactions on Medical Imaging, Jun. 1991, vol. 10, No. 2, 122-131.
Durali M, Shameli E. Full order neural velocity and acceleration observer for a general 6-6 Stewart platform. InNetworking, Sensing and Control, 2004 IEEE International Conference on Mar. 21, 2004 (vol. 1, pp. 333-338).
Decision to Grant (Translation) dated Mar. 2016 in Russian patent application 2012147835, 6 pages.
Charlton, an Investigation into the Effect of Lateral Hillslope inputs on Floorplain Hydraulic Model Predictions, Diss. University of Bristol, Sep. 1995, 289 pages.
Changjiang Yang et al: "Planar conic based camera calibration", Proceedings / 15th International Conference on Pattern Recognition Barcelona, Spain, Sep. 3-7, [Proceedings of the International Conference on Pattern Recognition. (ICPR)], IEEE Computer Society, Los Alamitos, CALIF. [U.A.], vol. 1, Sep. 3, 2000 (Sep. 3, 2000) pp. 555-558.
Circle Hough Transform, Wikipedia, https://en.wikipedia.org/wiki/Circle_Hough_Transform, web-archive capture from Jan. 23, 2020, accessed on Oct. 26, 2020 from web.archive.org/web/20200123161407/https://en.wikipedia.org/wiki/Circle_Hough_Transform, 5 pages.
Circle Hough Transform, Wikipedia, https://en.wikipedia.org/wiki/Circle_Hough_Transform, Dec. 1, 2019, webpage accessed Apr. 3, 2020, 5 pages.
Iterative Closest Point, Wikipedia, https://en.wikipedia.org/wiki/iterative_closest_point, web-archive capture from Jan. 17, 2019, accessed on Oct. 26, 2020 from web.archive.org/web/20190117001205/https://en.wikipedia.org/wiki/iterative_closest_point, 3 pages.
Iterative Closest Point, Wikipedia, https://en.wikipedia.org/wiki/iterative_closest_point, web-archive capture from Oct. 28, 2010, accessed on Oct. 26, 2020 from web.archive.org/web/20101028140305/https://en.wikipedia.org/wiki/iterative_closest_point, 3 pages.
Iterative Closest Point, Wikipedia, https://en.wikipedia.org/wiki/iterative_closest_point, web-archive capture from Sep. 13, 2006, accessed on Oct. 26, 2020 from web.archive.org/web/20060913000000/http://en.wikipedia.org/wiki/iterative_closest_point, 1 page.
Iterative Closest Point, Wikipedia, https://en.wikipedia.org/wiki/Iterative_closest_point, Mar. 19, 2020, webpage accessed Apr. 3, 2020, 3 pages.
Point set registration, Wikipedia, https://en.wikipedia.org/wiki/Point_set_registration, web-archive capture from Oct. 16, 2019, accessed on Oct. 26, 2020 from web.archive.org/web/2019016232144/https://en.wikipedia.org/wiki/Point_set-registration.
Point set registration, Wikipedia, https://en.wikipedia.org/wiki/Point_set_registration, Mar. 9, 2020, webpage accessed Apr. 3, 2020, 11 pages.

* cited by examiner

ORTHOPEDIC FIXATION WITH IMAGERY ANALYSIS

CROSS-REFERENCE TO RELATED APPLICATIONS

This application is a continuation of, and claims priority to, U.S. patent application Ser. No. 15/461,969, filed on Mar. 17, 2017, which is a divisional of, and claims priority to, U.S. patent application Ser. No. 13/111,180, filed on May 19, 2011, now issued as U.S. Pat. No. 9,642,649, which claims priority to Great Britain Patent Application Serial Number GB1008281.6, filed May 19, 2010. U.S. patent application Ser. No. 15/461,969, filed on Mar. 17, 2017, is incorporated herein by reference in its entirety. U.S. patent application Ser. No. 13/111,180, filed on May 19, 2011, is incorporated herein by reference in its entirety. Great Britain Patent Application Serial Number GB1008281.6, filed May 19, 2010, is incorporated herein by reference in its entirety.

BACKGROUND

Techniques used to treat bone fractures and/or bone deformities can include the use of external fixators, such as fixation frames, that are surgically mounted to bone segments on opposed sides of a fracture site. A pair of radiographic images is taken of the fixator and bone segments at the fracture site. Typically, the radiographic images must be orthogonal, or perpendicular with respect to each other and aligned with anatomical axes of the patient. Data from the images is then manipulated with orthogonal projection techniques to construct a three dimensional representation of the fixator and the bones segments that can be used in developing a treatment plan, which may for example comprise realigning the bone segments through adjustments to the fixator.

However, the ability to acquire orthogonal radiographic images of a fracture site can be limited by factors beyond a surgeon's control, for instance maneuverability of the imaging apparatus, the anatomical location of a fracture or deformity, and/or pain incurred by a patient in positioning a broken limb for orthogonal imaging. Limiting factors such as these can introduce inaccuracies into the imaging process. These inaccuracies can have undesirable consequences such as improper alignment of bone segments during the healing process, compromised union between the bone segments, necessitating additional rounds of radiographic imaging to facilitate alignment corrections, or even necessitating additional surgical procedures.

SUMMARY

In accordance with one embodiment, a method of orthopedic fixation includes attaching a fixation apparatus to first and second bone segments. The method further includes capturing a first image of the fixation apparatus and bone segments from a first orientation with respect to the fixation apparatus. The method further still includes capturing a second image of the fixation apparatus and bone segments from a second orientation with respect to the fixation apparatus that is different from the first orientation. The method further still includes computing first and second transformation matrices for the first and second images, respectively. The method further still includes utilizing the transformation matrices to reconstruct a three dimensional representation of the first and second bone segments with respect to the fixation apparatus.

In accordance with an alternative embodiment, a computer-readable storage medium has computer-readable instructions stored thereon that when executed by a processor perform a method of orthopedic fixation imagery analysis. The method includes capturing, via an imager, first and second images of a fixation apparatus and first and second bone segments attached thereto. The first image is captured from a first orientation and the second image is captured from a second orientation that is different from the first orientation. The method further includes obtaining a plurality of imaging scene parameters. The method further still includes reconstructing a three dimensional representation of the first and second bone segments with respect to the fixation apparatus based upon the plurality of imaging scene parameters.

BRIEF DESCRIPTION OF THE DRAWINGS

The foregoing summary, as well as the following detailed description of the preferred embodiments of the application, will be better understood when read in conjunction with the appended drawings. For the purposes of illustrating the methods and/or techniques of orthopedic fixation with imagery analysis, there are shown in the drawings preferred embodiments. It should be understood, however, that the instant application is not limited to the precise arrangements and/or instrumentalities illustrated in the drawings, in which.

DETAILED DESCRIPTION

Figure 1:
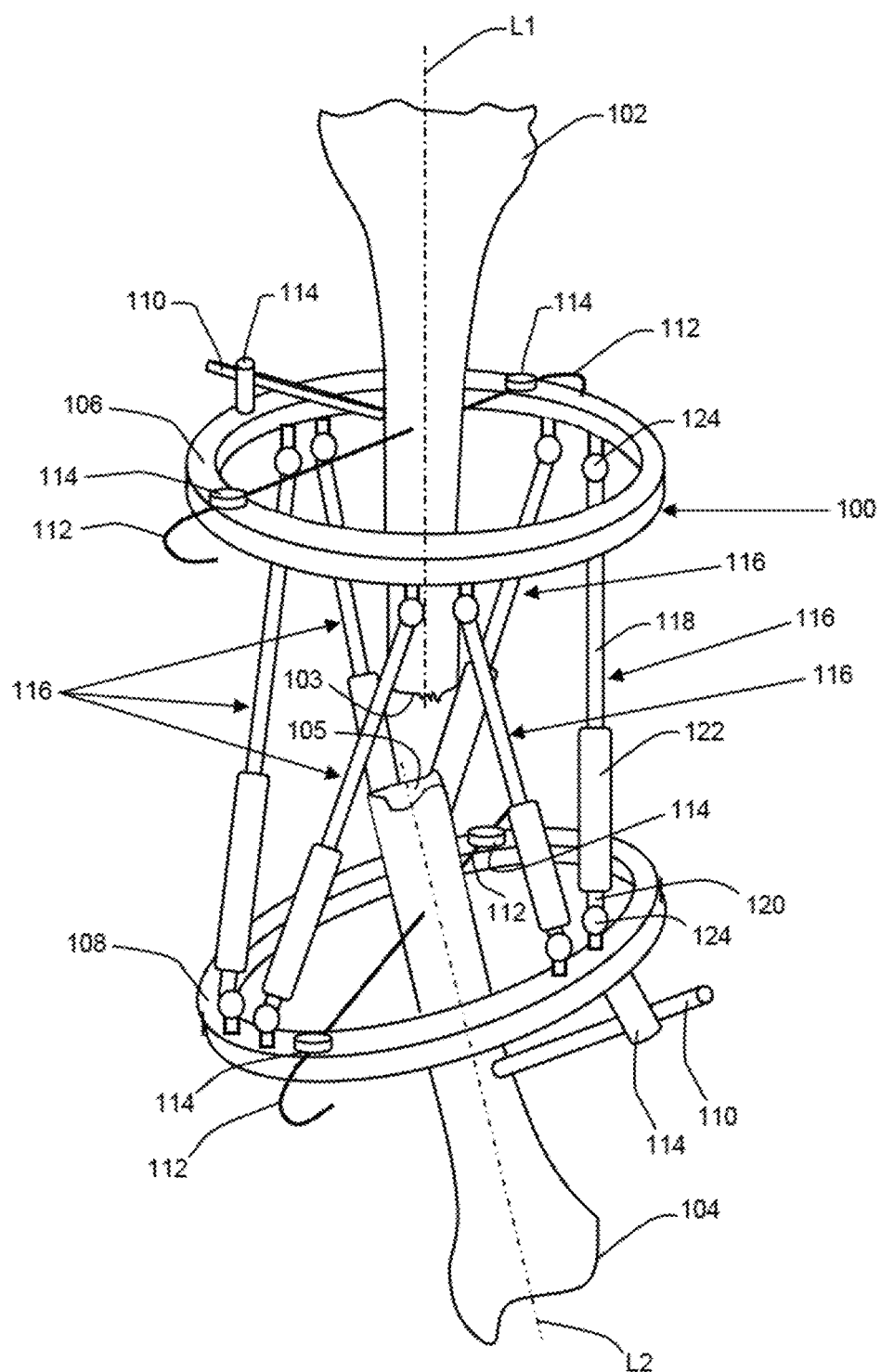
FIG. 1 is a perspective view of a fixation assembly positioned for imaging in accordance with an embodiment.

For convenience, the same or equivalent elements in the various embodiments illustrated in the drawings have been identified with the same reference numerals. Certain terminology is used in the following description for convenience only and is not limiting. The words "right", "left", "top" and "bottom" designate directions in the drawings to which reference is made. The words "inward", "inwardly", "outward", and "outwardly" refer to directions toward and away from, respectively, the geometric center of the device and designated parts thereof. The terminology intended to be non-limiting includes the above-listed words, derivatives thereof and words of similar import.

Referring initially to FIG. 1, bodily tissues, for instance first and second bone segments 102, 104, can be aligned and/or oriented to promote union or other healing between the bodily tissues. The alignment and/or orientation of the bodily tissues can be achieved by connecting the bodily tissues to an adjustable fixation apparatus, such as orthopedic fixator 100. The orthopedic fixator can comprise an external fixation apparatus that includes a plurality of discrete fixator members that remain external to the patient's body, but that are attached to respective discreet bodily tissues, for example with minimally invasive attachment members. By adjusting the spatial positioning of the fixator members with respect to each other, the respective bodily tissues attached thereto can be reoriented and/or otherwise brought into alignment with each other, for example to promote union between the bodily tissues during the healing process. The use of external orthopedic fixators in combination with the imagery analysis and positioning techniques described herein can be advantageous in applications where direct measurement and manipulation of the bodily tissues is not possible, where limited or minimally invasive access to the bodily tissues is desired, or the like.

The fixator members can be connected to each other via adjustment members, the adjustment members configured to facilitate the spatial repositioning of the fixator members with respect to each other. For example, in the illustrated embodiment, the orthopedic fixator 100 comprises a pair of fixator members in the form of an upper fixator ring 106 and a lower fixator ring 108. The fixator rings 106, 108 can be constructed the same or differently. For instance, the fixator rings 106, 108 can have diameters that are the same or different. Similarly, the fixator rings 106, 108 can be constructed with varying cross sectional diameters, thicknesses, etc. It should be appreciated that the fixator members of the orthopedic fixator 100 are not limited to the illustrated upper and lower fixator rings 106, 108, and that the orthopedic fixator 100 can be alternatively constructed. For example, additional fixator rings can be provided and interconnected with the fixator ring 106 and/or 108. It should further be appreciated that the geometries of the fixator members are not limited to rings, and that at least one, such as all of the fixator members can be alternatively constructed using any other suitable geometry.

The first and second bone segments 102, 104 can be rigidly attached to the upper and lower fixator rings 106, 108, respectively, with attachment members that can be mounted to the fixator rings 106, 108. For example, in the illustrated embodiment, attachment members are provided in the form of attachment rods 110 and attachment wires 112.

The rods 110 and the wires 112 extend between proximal ends attached to mounting members 114 that are mounted to the fixator rings 106, 108, and opposed distal ends that are inserted into or otherwise secured to the bone segments 102, 104. The mounting members 114 can be removably mounted to the fixator rings 106, 108 at predefined points along the peripheries of the fixator rings 106, 108, for example by disposing them into threaded apertures defined by the fixator rings. With respect to each fixator ring 106, 108, the mounting members 114 can be mounted to the upper surface of the ring, the lower surface of the ring, or any combination thereof. It should be appreciated that the attachment members are not limited to the configuration of the illustrated embodiment. For example, any number of attachment members, such as the illustrated rods 110 and wires 112 and any others, can be used to secure the bone segments to respective fixator members as desired. It should further be appreciated that one or more of the attachment members, for instance the rods 110 and/or wires 112, can be alternatively configured to mount directly to the fixator rings 106, 108, without utilizing mounting members 114.

The upper and lower fixator rings 106, 108 can be connected to each other by at least one, such as a plurality of adjustment members. At least one, such as all, of the adjustment members can be configured to allow the spatial positioning of the fixator rings with respect to each other to be adjusted. For example, in the illustrated embodiment, the upper and lower fixator rings 106, 108 are connected to each other with a plurality of adjustment members provided in the form of adjustable length struts 116. It should be appreciated that the construction of the orthopedic fixator 100 is not limited to the six struts 116 of the illustrated embodiment, and that more or fewer struts can be used as desired.

Each of the adjustable length struts 116 can comprise opposed upper and lower strut arms 118, 120. Each of the upper and lower strut arms 118, 120 have proximal ends disposed in a coupling member, or sleeve 122, and opposed distal ends that are coupled to universal joints 124 mounted to the upper and lower fixator rings 106, 108, respectively. The universal joints of the illustrated embodiment are disposed in pairs spaced evenly around the peripheries of the upper and lower fixator rings 106, 108, but can be alternatively placed in any other locations on the fixator rings as desired.

The proximal ends of the upper and lower strut arms 118, 120 of each strut 116 can have threads defined thereon that are configured to be received by complementary threads defined in the sleeve 122, such that when the proximal ends of the upper and lower strut arms 118, 120 of a strut 116 are received in a respective sleeve 122, rotation of the sleeve 122 causes the upper and lower strut arms 118, 120 to translate within the sleeve 122, thus causing the strut 116 to be elongated or shortened, depending on the direction of rotation. Thus, the length of each strut 116 can be independently adjusted with respect to the remaining struts. It should be appreciated that the adjustment members are not limited to the length adjustable struts 116 of the illustrated embodiment, and that the adjustment members can be alternatively constructed as desired, for example using one or more alternative geometries, alternative length adjustment mechanisms, and the like.

The adjustable length struts 116 and the universal joints 124 by which they are mounted to the upper and lower fixator rings 106, 108, allow the orthopedic fixator 100 to function much like a Stewart platform, and more specifically like a distraction osteogenesis ring system, a hexapod, or a Taylor spatial frame. That is, by making length adjustments to the struts 116, the spatial positioning of the upper and lower fixator rings 106, 108, and thus the bone segments 102, 104 can be altered. For example, in the illustrated embodiment the first bone segment 102 is attached to the upper fixator ring 106 and the second bone segment 104 is attached to the lower fixator ring 108. It should be appreciated that attachment of the first and second bone segments 102, 104 to the upper and lower fixator rings 106, 108 is not limited to the illustrated embodiment (e.g., where the central longitudinal axes L1, L2 of the first and second bone segments 102, 104 are substantially perpendicular to the respective planes of the upper and lower fixator rings 106, 108), and that a surgeon has complete flexibility in aligning the first and second bone segments 102, 104 within the upper and lower fixator rings 106, 108 when configuring the orthopedic fixator 100.

By varying the length of one or more of the struts 116, the upper and lower fixator rings 106, 108, and thus the bone segments 102 and 104 can be repositioned with respect to each other such that their respective longitudinal axes L1, L2 are substantially aligned with each other, and such that their respective fractured ends 103, 105 abut each other, so as to promote union during the healing process. It should be appreciated that adjustment of the struts 116 is not limited to the length adjustments as described herein, and that the struts 116 can be differently adjusted as desired. It should further be appreciated that adjusting the positions of the fixator members is not limited to adjusting the lengths of the length adjustable struts 116, and that the positioning of the fixator members with respect to each other can be alternatively adjusted, for example in accordance the type and/or number of adjustment members connected to the fixation apparatus.

Repositioning of the fixator members of an orthopedic fixation apparatus, such as orthopedic fixator 100, can be used to correct displacements of angulation, translation, rotation, or any combination thereof, within bodily tissues. A fixation apparatus, such as orthopedic fixator 100, utilized with the techniques described herein, can correct a plurality of such displacement defects individually or simultaneously. However, it should be appreciated that the fixation apparatus is not limited to the illustrated orthopedic fixator 100, and that the fixation apparatus can be alternatively constructed as desired. For example, the fixation apparatus can include additional fixation members, can include fixation members having alternative geometries, can include more or fewer adjustment members, can include alternatively constructed adjustment members, or any combination thereof.

Figure 2:
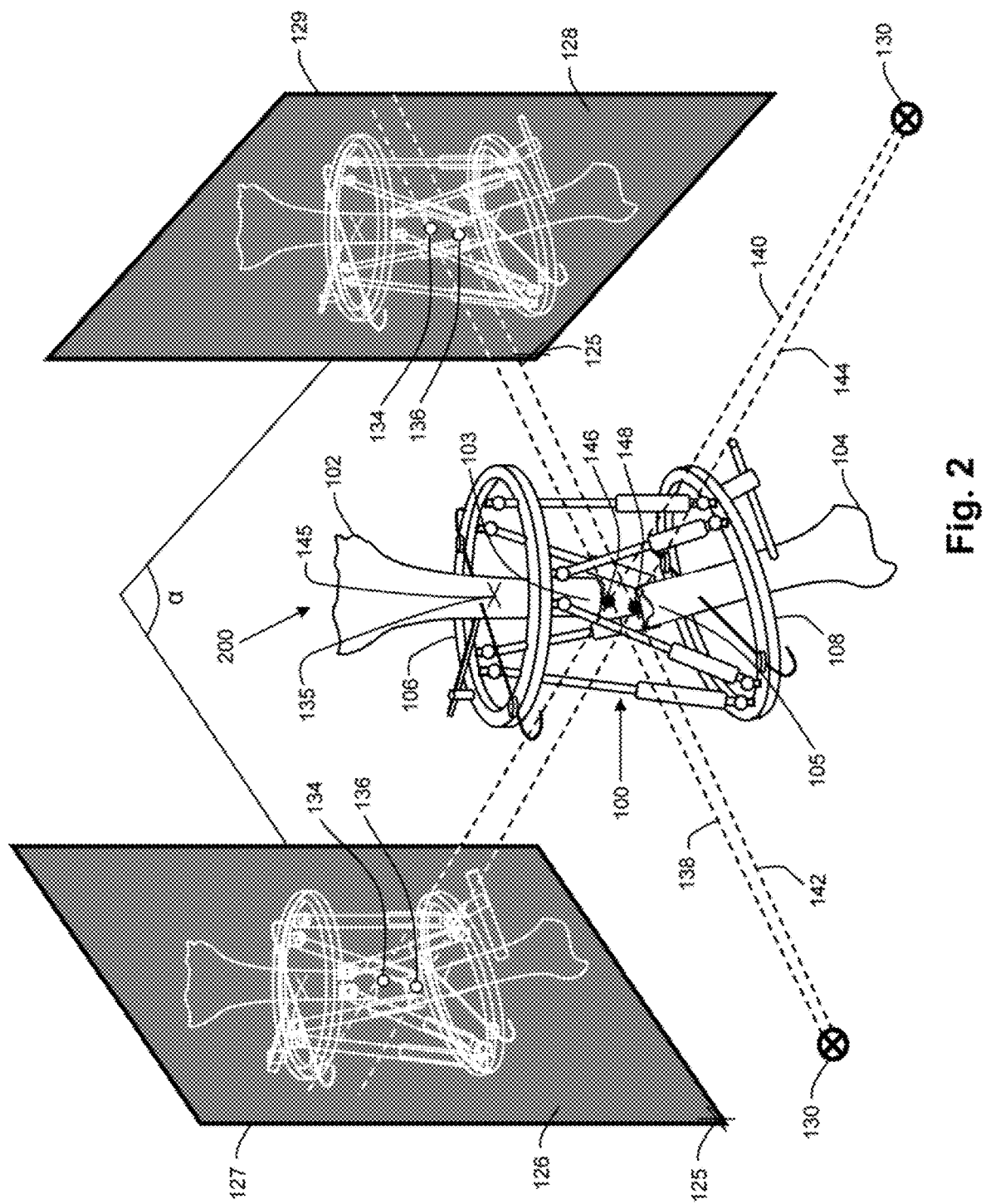
FIG. 2 is a perspective view of an example imaging process of the fixation assembly illustrated in FIG. 1.
Figure 3:
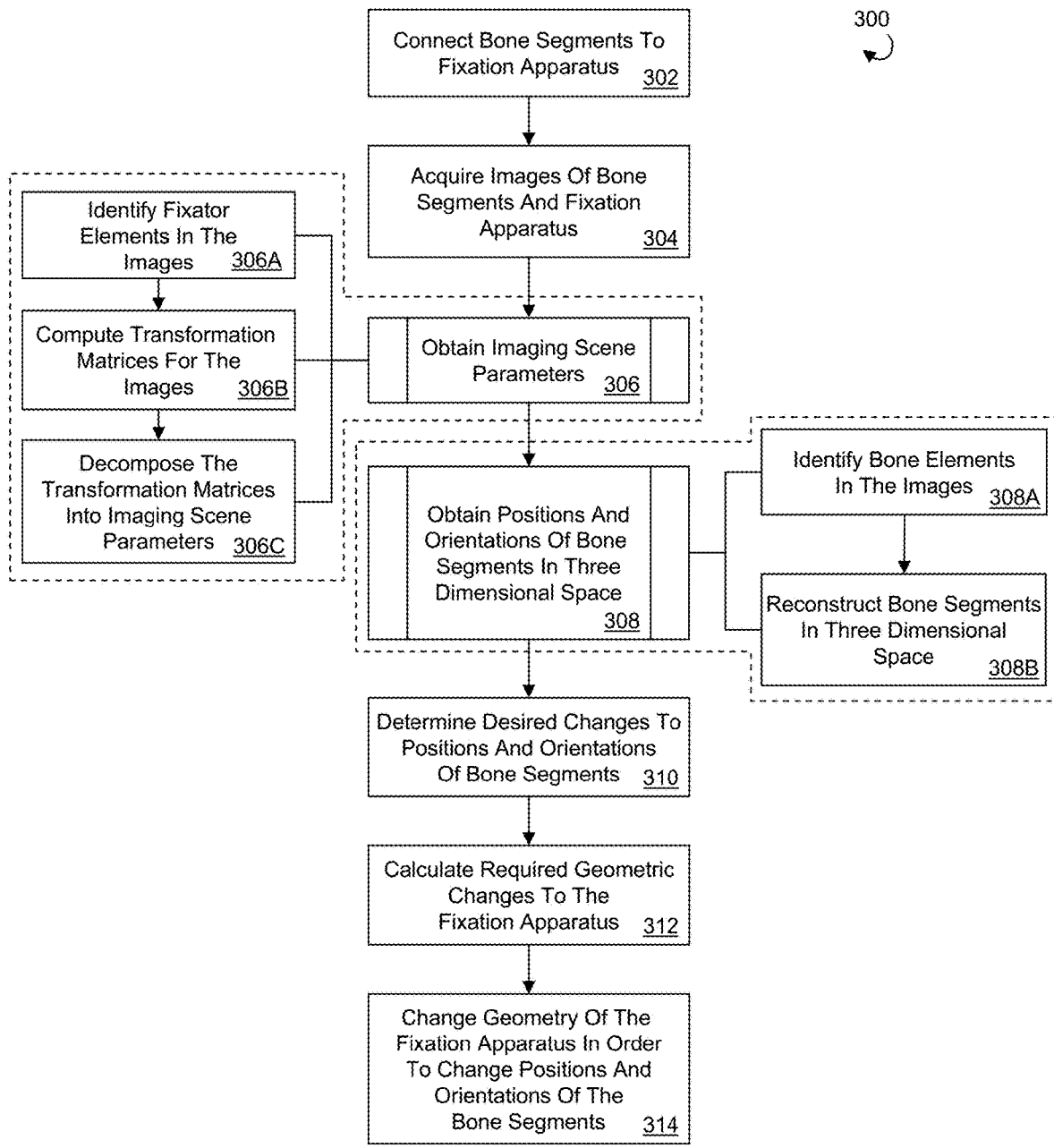
FIG. 3 is a flow diagram illustrating an example orthopedic fixation with imagery analysis process in accordance with an embodiment.

Referring now to FIGS. 2-3, an example orthopedic fixation with imagery analysis process, or method in accordance with an embodiment is illustrated. Steps for carrying out an example orthopedic fixation with imagery analysis method 300 are depicted in the flow chart of FIG. 3. At step 302, bodily tissues, such as first and second bone segments 102, 104, can be connected to an adjustable fixation apparatus, such as the orthopedic fixator 100, as described above.

At step 304, with the orthopedic fixator 100 secured to the bone segments 102, 104, at least one, such as a plurality of images can be taken of the fixator 100 and the bone segments 102, 104. The images can be captured using the same or different imaging techniques. For example, the images can be acquired using x-ray imaging, computer tomography, magnetic resonance imaging, ultrasound, infrared imaging, photography, fluoroscopy, visual spectrum imaging, or any combination thereof.

The images can be captured from any position and/or orientation with respect to each other and with respect to the fixator 100 and the bone segments 102, 104. In other words, there is no requirement that the captured images be orthogonal with respect to each other or aligned with anatomical axes of the patient, thereby providing a surgeon with near complete flexibility in positioning the imagers 130. Preferably, the images 126, 128 are captured from different directions, or orientations, such that the images do not overlap. For example, in the illustrated embodiment, the image planes of the pair of images 126, 128 are not perpendicular with respect to each other. In other words, the angle α between the image planes of the images 126, 128 is not equal to 90 degrees, such that the images 126, 128 are non-orthogonal with respect to each other. Preferably, at least two images are taken, although capturing additional images may increase the accuracy of the method.

The images 126, 128 can be captured using one or more imaging sources, or imagers, for instance the x-ray imagers 130 and/or corresponding image capturing devices 127, 129. The images 126, 128 can be x-ray images captured by a single repositionable x-ray imager 130, or can be captured by separately positioned imagers 130. Preferably, the position of the image capturing devices 127, 129 and/or the imagers 130 with respect to the space origin 135 of the three dimensional space, described in more detail below, are known. The imagers 130 can be manually positioned and/or oriented under the control of a surgeon, automatically positioned, for instance by a software assisted imager, or any combination thereof.

At step 306, imaging scene parameters pertaining to fixator 100, the bone segments 102, 104, imager(s) 130, and image capturing devices 127, 129 are obtained. The imaging scene parameters can be used in constructing a three dimensional representation of the positioning of the bone segments 102, 104 in the fixator 100, as described in more detail below. One or more of the imaging scene parameters may be known. Imaging scene parameters that are not known can be obtained, for example by mathematically comparing the locations of fixator element representations in the two dimensional space of the x-ray images 126, 128 to the three dimensional locations of those elements on the geometry of the fixator 100. In a preferred embodiment, imaging scene parameters can be calculated using a pin hole or perspective camera models. For example, the imaging scene parameters can be determined numerically using matrix algebra, as described in more detail below.

The imaging scene parameters can include, but are not limited to image pixel scale factors, image pixel aspect ratio, the image sensor skew factor, the image size, the focal length, the position and orientation of the imaging source, the position of the principle point (defined as the point in the plane of a respective image 126, 128 that is closest to the respective imager 130), positions and orientations of elements of the fixator 100, the position and orientation of a respective image receiver, and the position and orientation of the imaging source's lens.

In a preferred embodiment, at least some, such as all of the imaging scene parameters can be obtained by comparing the locations of representations of particular components, or fixator elements of the fixator 100 within the two dimensional spaces of the images 126, 128, with the corresponding locations of those same fixator elements in actual, three dimensional space. The fixator elements comprise components of the orthopedic fixator 100, and preferably are components that are easy to identify in the images 126, 128. Points, lines, conics, or the like, or any combination thereof can be used to describe the respective geometries of the fixator elements. For example, the representations of fixator elements used in the comparison could include center lines of one or more of the adjustable length struts 116, center points of the universal joints 124, center points of the mounting members 114, and the like.

The fixator elements can further include marker elements that are distinct from the above-described components of the fixator 100. The marker elements can be used in the comparison, as a supplement to or in lieu of using components of the fixator 100. The marker elements can be mounted to specific locations of components of the fixator 100 prior to imaging, can be imbedded within components of the fixator 100, or any combination thereof. The marker elements can be configured for enhanced viewability in the images 126, 128 when compared to the viewability of the other components of the fixator 100. For example, the marker elements may be constructed of a different material, such as a radio-opaque material, or may be constructed with geometries that readily distinguish them from other components of the fixator 100 in the images 126, 128. In an example embodiment, the marker elements can have designated geometries that correspond to their respective locations on the fixator 100.

At step 306A, fixator elements can be identified for use in the comparison. The identification of fixator elements and the determination of their respective locations can be performed by a surgeon, with the assistance of software, or by any combination thereof.

The locations of the fixator elements in the two dimensional space of the images 126, 128 are determined with respect to local origins 125 defined in the imaging planes of the images 126, 128. The local origins 125 serve as a "zero points" for determining the locations of the fixator elements in the images 126, 128. The locations of the fixator elements can be defined by their respective x and y coordinates with respect to a respective local origin 125. The location of the local origin 125 within the respective image can be arbitrary so long it is in the plane of the image. Typically, the origin is located at the center of the image or at a corner of the image, such as the lower left hand corner. It should be appreciated that the locations of the local origins are not limited to illustrated local origins 125, and that the local origins 125 can be alternatively defined at any other locations. It should further be appreciated that the locations of the local origins 125 can be designated by a surgeon, with the assistance of software, or by any combination thereof.

At step 306B, a respective transformation matrix P can be computed for each of the images 126, 128. The transformation matrices can be utilized to map location coordinates of one or more respective fixator elements in actual three dimensional space to corresponding location coordinates of the fixator element(s) in the two dimensional space of the respective image 126, 128. It should be appreciated that the same fixator element(s) need not be used in the comparisons of both images 126, 128. For example, a fixator element used in constructing the transformation matrix associated with image 126 can be the same or different from the fixator element used in constructing the transformation matrix associated with image 128. It should further be appreciated that increasing the number of fixator elements used in computing the transformation matrices can increase the accuracy method. The following equation represents this operation:

$$\begin{bmatrix} x \\ y \\ 1 \end{bmatrix} = P \cdot \begin{bmatrix} X \\ Y \\ Z \\ 1 \end{bmatrix} \quad (1)$$

The symbols x and y represent location coordinates, with respect to the local origin 125, of a fixator element point in the two dimensional space of images 126, 128. The symbols X, Y and Z represent corresponding location coordinates, with respect to a space origin 135, of the fixator element point in actual three dimensional space. In the illustrated embodiment, the point corresponding to the center of the plane defined by the upper surface of the upper fixator ring 106 has been designated as the space origin 135. The illustrated matrix P can be at least four elements wide and three elements tall. In a preferred embodiment, the elements of the matrix P can be computed by solving the following matrix equation:

$$A \cdot p = B \quad (2)$$

The vector p can contain eleven elements representing values of the matrix P. The following equations present arrangements of the elements in the vector p and the matrix P:

$$p = [\, p_1 \;\; p_2 \;\; p_3 \;\; p_4 \;\; p_5 \;\; p_6 \;\; p_7 \;\; p_8 \;\; p_9 \;\; p_{10} \;\; p_{11} \,]^T \quad (3)$$

$$P = \begin{bmatrix} p_1 & p_2 & p_3 & p_4 \\ p_5 & p_6 & p_7 & p_8 \\ p_9 & p_{10} & p_{11} & p_{12} \end{bmatrix} \quad (4)$$

In the preferred embodiment, the twelfth element $p_{12}$ of the matrix P can be set to a numerical value of one. The matrices A and B can be assembled using the two dimensional and three dimensional information of the fixator elements. For every point representing a respective fixator element, two rows of matrices A and B can be constructed. The following equation presents the values of the two rows added to the matrices A and B for every point of a fixator element (e.g., a center point of a respective universal joint 124):

$$\begin{bmatrix} \ldots & \ldots & \ldots & \ldots & \ldots & \ldots & \ldots & \ldots & \ldots & \ldots & \ldots \\ X & Y & Z & 1 & 0 & 0 & 0 & 0 & -x \cdot X & -x \cdot Y & -x \cdot Z \\ 0 & 0 & 0 & 0 & X & Y & Z & 1 & -x \cdot X & -x \cdot X & -x \cdot X \\ \ldots & \ldots & \ldots & \ldots & \ldots & \ldots & \ldots & \ldots & \ldots & \ldots & \ldots \end{bmatrix} \cdot p = \begin{bmatrix} \ldots \\ x \\ y \\ \ldots \end{bmatrix} \quad (5)$$

The symbols X, Y and Z represent location coordinate values of a fixator element point in actual three dimensional space relative to the space origin 135, and the symbols x and y represent location coordinate values of the corresponding fixator element point in the two dimensional space of the respective image 126, 128 relative to local origin 125.

For every line representing a respective fixator element, two rows of matrices A and B can be constructed. The following equation presents the values of the two rows added to the matrices A and B for every line of a fixator element (e.g., a center line of a respective adjustable length strut 116):

$$\begin{bmatrix} \ldots & \ldots & \ldots & \ldots & \ldots & \ldots & \ldots & \ldots & \ldots & \ldots & \ldots \\ X \cdot a & Y \cdot a & Z \cdot a & a & X \cdot b & Y \cdot b & Z \cdot b & b & X \cdot c & Y \cdot c & Z \cdot c \\ dX \cdot a & dY \cdot a & dZ \cdot a & 0 & dX \cdot b & dY \cdot b & dZ \cdot b & 0 & dY \cdot c & dY \cdot c & dZ \cdot c \\ \ldots & \ldots & \ldots & \ldots & \ldots & \ldots & \ldots & \ldots & \ldots & \ldots & \ldots \end{bmatrix} \cdot p = \begin{bmatrix} \ldots \\ -c \\ 0 \\ \ldots \end{bmatrix} \quad (6)$$

The symbols X, Y and Z represent location coordinate values of a point belonging to a line of a fixator element in actual three dimensional space relative to the space origin 135. The symbols dX, dY and dZ represent gradient values of the line in actual three dimensional space. The symbols a, b and c represent constants defining a line in the two dimensional space of a respective image 126, 128. For example, a, b, and c can be computed using two points belonging to a line on a respective image 126, 128. In a preferred embodiment, the value of b is assumed to be 1, unless the line is a vertical line, in which case the value of b is zero. A correlation of constants a, b and c with the respective image coordinates x and y is presented in the following equation:

$$a \cdot x + b \cdot y + c = 0 \quad (7)$$

The equation (2) can be over constrained by using six or more fixator elements, for example the adjustable length struts 116. It should be appreciated that it is not necessary for all of the fixator elements to be visible in a single one of the images 126, 128 in order to obtain the matrix P. It should further be appreciated that if one or more of the above-described imaging scene parameters are known, the known parameters can be used to reduce the minimum number of the fixator elements required to constrain equation (2). For instance, such information could be obtained from modern imaging systems in DICOM image headers. Preferably, a singular value decomposition or least squares method can be used to solve equation (2) for values of the vector p.

At step 306C, the transformation matrices can be decomposed into imaging scene parameters. The following equation can be used to relate the matrix P to matrices E and I:

$$P = I \cdot E \quad (8)$$

It should be appreciated that additional terms can be introduced when decomposing the matrix P. For example, the method presented by Tsai, described in "A Versatile Camera Calibration Technique for High-Accuracy 3D Machine Vision Metrology Using of-the-shelf TV Cameras and Lenses", IEEE Journal of Robotics & Automation, RA-3, No. 4, 323-344, August 1987, which is incorporated herein by reference in its entirety, can be used to correct images 126, 128, for radial distortion.

Matrices E and I contain imaging scene parameters. The following equation represents a composition of the matrix I:

$$I = \begin{bmatrix} sx & 0 & -tx \\ 0 & sy & -ty \\ 0 & 0 & 1/f \end{bmatrix} \quad (9)$$

The symbols sx and sy represent values of image coordinate scale factors (e.g., pixel scale factors). The symbol f, representing the focal length, corresponds to the value of the shortest distance between a respective imaging source 130 and the plane of a corresponding image 126, 128. The symbols tx and ty represent the coordinates of the principle point relative to the local origin 125 of the respective image 126, 128. The following equation represents the composition of the matrix E:

$$E = \begin{bmatrix} r_1 & r_2 & r_3 & -(r_1 \cdot o_x + r_2 \cdot o_y + r_3 \cdot o_z) \\ r_4 & r_5 & r_6 & -(r_4 \cdot o_x + r_5 \cdot o_y + r_6 \cdot o_z) \\ r_7 & r_8 & r_9 & -(r_7 \cdot o_x + r_8 \cdot o_y + r_9 \cdot o_z) \end{bmatrix} \quad (10)$$

The symbols $o_x$, $o_y$ and $o_z$ represent values of the position of the fixator 100 in actual three dimensional space. The symbols $r_1$ to $r_9$ describe the orientation of the fixator 100. These values can be assembled into a three dimensional rotational matrix R represented by the following equation:

$$R = \begin{bmatrix} r_1 & r_2 & r_3 \\ r_4 & r_5 & r_6 \\ r_7 & r_8 & r_9 \end{bmatrix} \quad (11)$$

The methods of Trucco and Verri, as described in "Introductory Techniques of 3-D Computer Vision", Prentice Hall, 1998, or the method of Hartley, as described in "Euclidian Reconstruction from Uncalibrated Views", Applications of Invariance in Computer Vision, pages 237-256, Springer Verlag, Berlin Heidelberg, 1994, which are incorporated herein in their entireties, can be used to obtain values of the matrices E and/or I. Utilizing the resulting values of matrices E and I, a complete three dimensional imaging scene of the fixator 100 and the bone segments 102, 104 can be reconstructed.

For example, FIG. 2 illustrates an example three dimensional imaging scene reconstructed from the x-ray images 126, 128. In the illustrated embodiment, x-rays are emitted from x-ray imagers 130. It should be appreciated that the x-ray imagers 130 can be the same or different imagers, as described above. The x-rays emitted from the imagers 130 are received on by corresponding imaging devices, thus capturing the images 126, 128. Preferably, the positioning of the imagers 130 with respect to the local origins 125 is known.

At step 308, the images 126, 128 and the imaging scene parameters can be used to obtain the positions and/or orientations of the bone segments 102, 104 in three dimensional space. The position and/or orientation data obtained can be used to develop a treatment plan for a patient, for example to change the orientation and/or position of the fractured first and second bone segments 102, 104 in order to promote union between the bone segments 102, 104, as described in more detail below. It should be appreciated that the methods and techniques of orthopedic fixation with imagery analysis described herein are not limited to applications of repositioning broken bones, and that orthopedic fixation with imagery analysis can be used in any other type of fixation procedure as desired, for example lengthening of bones, correction of anatomical defects, and the like.

At step 308A, bone elements comprising representations of particular portions (e.g., anatomical features) of the bone segments 102, 104, can be identified and their locations within the images 126, 128 determined. Preferably, the locations of the bone elements are determined with respect to the respective local origins 125 of images 126, 128. The identification of the bone elements and the determination of their respective locations can be performed by a surgeon, with the assistance of software, or by any combination thereof.

The bone elements can be used in the construction of the three dimensional representation of the position and/or orientation of the bone segments 102, 104. Preferably, the bone elements are easy to identify in the images 126, 128. Points, lines, conics, or the like, or any combination thereof can be used to describe the respective geometries of the bone elements. For example, in the illustrated embodiment, points 134 and 136 representing the fractured ends 103, 105 of the bone segments 102, 104, respectively, are identified as bone elements in the images 126, 128.

The bone elements can further include marker elements that are implanted into the bone segments 102, 104 prior to imaging. The marker elements can be used as a supplement to or in lieu of the above-described bone elements identified in the images 124, 126. The marker elements can be configured for enhanced viewability in the images 126, 128 when compared to the viewability of anatomical features of the bone segments 102, 104. For example, the marker elements may be constructed of a radio-opaque material, or may be constructed with readily distinguishable geometries.

At step 308B, a three dimensional representation 200 of the bone segments 102, 104 can be reconstructed. The three dimensional representation can be constructed with or without a corresponding representation of the fixator 100. In the illustrated embodiment, pairs of ray-lines, such as ray lines 138, 140 and 142, 144 can be constructed for the bone element points 134, 136, respectively. Each ray line connects a bone element in one of the images 126, 128 with a respective imager 130. Each pair of ray lines can be analyzed for a common intersection point, such as points 146, 148. The common intersection points 146, 148 represent the respective positions of the bone element points 134, 136, in the three dimensional representation of the bone segments 102, 104. Of course more than a pair of ray lines, such as a plurality, can be constructed, for example if more than two images were captured. If the ray lines of a particular set do not intersect, a point closest to all the ray lines in the set can be used as the common intersection point.

The positions and/or orientations of the bone segments 102, 104 can be quantified or measured using common intersection points, for instance points 146, 148. For example, lines representing center lines of the bone segments 102, 104 can be constructed and can be compared to the anatomical axes of the patient. Additionally, the distance between the fractured ends 103, 105 of the bone segments 102, 104 can be quantified. Using these or similar techniques, the positions and/or orientations of the bone segments 102, 104 can be determined.

At step 310, the three dimensional representation 200 can be used to determine desired changes to the positions and/or orientations of the bone segments 102, 104, for instance how the bone segments 102, 104 can be repositioned with respect to each other in order to promote union between the bone segments 102, 104. For example, in the illustrated embodiment, it may be desirable to change the angulation of the second bone segment 104 such that the axes L1 and L2 are brought into alignment, and to change the position of the second bone segment such that the fractured ends 103, 105 of the bone segments 102, 104 abut each other. Preferably, the determination of the desired changes to the positions and/or orientations of the bone segments 102, 104 are made by a surgeon. In an example embodiment, lines representing the longitudinal axes L1, L2 of the first and second bone segments 102, 104 can be generated in the three dimensional representation, in order to aid in determining desired changes to the positions and/or orientations of the bone segments 102, 104. In determining the desired changes to the positions and/or orientations of the bone segments, the surgeon may be aided by software, such as a computer program configured to determine the desired positions and/or orientations of the bone segments 102, 104. Preferably, the desired changes to the positions and/or orientations of the bone segments 102, 104 are defined relative to the space origin 135.

Once the desired changes to the positions and/or orientations of the bone segments 102, 104 have been determined, a treatment plan for effecting the position and/or orientation changes can be determined. In a preferred embodiment, the desired changes to the positions and/or orientations of the bone segments 102, 104 can be effected gradually, in a series of smaller changes. The positions and/or orientations of the bone segments 102, 104 can be changed by changing the positions and/or orientations of the upper and lower fixator rings 106, 108 with respect to each other, for instance by lengthening or shortening one or more of the length adjustable struts 116.

At step 312, the required changes to the geometry of the fixator 100 (i.e., the position and/or orientation of the fixator 100) that can enable the desired changes to the positions and/or orientations of the bone segments 102, 104 can be computed using the matrix algebra described above. For example, the required repositioning and/or reorientation of the second bone segment 104 with respect to the first bone segment 102 can be translated to changes in the position and/or orientation of the lower fixator ring 108 with respect to the upper fixator ring 106. The required changes to the geometry of the fixator can be expressed with respect to a fixator origin 145 designated for the orthopedic fixator 100. It should be appreciated that the fixator origin 145 need not coincide with the space origin 135, as depicted in the illustrated embodiment.

At step 314, the treatment plan can be implemented, that is the positions and/or orientations of the bone segments 102, 104 can be altered by changing the geometry of the fixator 100.

As described above, one or more of the methods steps described herein and illustrated in FIG. 3 can be executed by a computer program, software, firmware or other form of computer-readable instructions incorporated in a computer-readable medium for execution by a computer or processor. Examples of computer-readable media can include computer-readable storage media and computer-readable communication media. Examples of computer-readable storage media include, but are not limited to, a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs). Examples of computer-readable communication media include, but are not limited to electronic signals transmitted over wired or wireless connections.

It should be appreciated that the orthopedic fixation with imagery analysis techniques described herein provide not only for the use of non-orthogonal images, but also allow the use of overlapping images, images captured using different imaging techniques, images captured in different settings, and the like, thereby presenting a surgeon with greater flexibility when compared with existing fixation and imagery techniques.

It should further be appreciated that the methods and techniques described herein with respect to orthopedic fixation can also be applied to other uses. For example, a repositionable mechanical manipulation apparatus, such as a parallel manipulator, a Stewart platform, or the like, can have first and second objects connected to it. The manipulation apparatus can be made up of a plurality of components. The first and second objects can be any objects that are to be repositioned and/or realigned with respect to each other. Steps similar to those of the orthopedic fixation with imagery analysis method 300 can be applied to reconstruct a three dimensional representation of the first and second objects with respect to the repositionable manipulation apparatus. A three dimensional representation of the first and second objects can be reconstructed and used to determine one or more geometry changes of the manipulation apparatus that when implemented can reposition the first and second objects with respect to each other. The three dimensional representation can be reconstructed using respective first and second pluralities of imaging scene parameters, a location of an element of at least one of the objects in the first image, and a location of an element of at least one of the objects in the second image.

Although the orthopedic fixation with imagery analysis techniques have been described herein with reference to preferred embodiments and/or preferred methods, it should be understood that the words which have been used herein are words of description and illustration, rather than words of limitation, and that the scope of the instant disclosure is not intended to be limited to those particulars, but rather is meant to extend to all structures, methods, and/or uses of the herein described orthopedic fixation with imagery analysis techniques. Those skilled in the relevant art, having the benefit of the teachings of this specification, may effect numerous modifications to the orthopedic fixation with imagery analysis techniques as described herein, and changes may be made without departing from the scope and spirit of the instant disclosure, for instance as recited in the appended claims.

What is claimed:

1. One or more non-transitory computer-readable storage media having stored thereon instructions that, upon execution by one or more computing devices, cause the one or more computing devices to perform operations comprising:
   acquiring first and second two-dimensional images of a fixation apparatus and first and second bone segments attached thereto, wherein the first two-dimensional image is captured from a first orientation and the second two-dimensional image is captured from a second orientation that is different from the first orientation;
   obtaining imaging scene parameters based in part on respective locations of a plurality of fixator elements in the first and the second two-dimensional images, the plurality of fixator elements having corresponding physical locations in three-dimensional space, wherein the obtaining of the imaging scene parameters comprises identifying, based at least in part on a first conic that describes one or more geometries of at least a fixator ring of the plurality of fixator elements, the respective locations of the plurality of fixator elements in the first and the second two-dimensional images; and
   reconstructing a three dimensional representation of the first and the second bone segments with respect to the fixation apparatus based upon the imaging scene parameters.

2. The one or more non-transitory computer-readable storage media of claim 1, wherein the identifying is based at least in part on a plurality of conics comprising the first conic and a second conic.

3. The one or more non-transitory computer-readable storage media of claim 2, wherein the second conic describes one or more other geometries of one or more other fixator elements of the plurality of fixator elements.

4. The one or more non-transitory computer-readable storage media of claim 1, wherein the first and the second orientations are not orthogonal with respect to each other.

5. The one or more non-transitory computer-readable storage media of claim 1, wherein the obtaining of the imaging scene parameters is based on a comparison of the respective locations of the plurality of fixator elements in the first and the second two-dimensional images with the corresponding physical locations of the plurality of fixator elements in three-dimensional space, and wherein the operations further comprise:
   constructing first and second transformation matrices corresponding to the first and second two-dimensional images, respectively, using the respective locations of the plurality of fixator elements; and
   decomposing the first and the second transformation matrices into the imaging scene parameters.

6. The one or more non-transitory computer-readable storage media of claim 5, wherein the constructing of the first and the second transformation matrices is based at least in part on one or more lines representing at least one of the plurality of fixator elements.

7. The one or more non-transitory computer-readable storage media of claim 6, wherein the constructing of the first and the second transformation matrices comprises constructing rows of matrices based on the one or more lines.

8. The one or more non-transitory computer-readable storage media of claim 6, wherein the constructing of the first and the second transformation matrices is based, at least in part, on a point value and a gradient value for each of the one or more lines.

9. The one or more non-transitory computer-readable storage media of claim 1, wherein the operations further comprise identifying respective locations of a plurality of bone elements in the first and the second two-dimensional images, the plurality of bone elements comprising anatomical features of the first and the second bone segments.

10. A computer-implemented method of orthopedic fixation imagery analysis, the computer-implemented method comprising:
    acquiring, by one or more computing devices, first and second two-dimensional images of a fixation apparatus and first and second bone segments attached thereto, wherein the first two-dimensional image is captured from a first orientation and the second two-dimensional image is captured from a second orientation that is different from the first orientation;
    obtaining, by the one or more computing devices, imaging scene parameters based in part on respective locations of a plurality of fixator elements in the first and the second two-dimensional images, the plurality of fixator elements having corresponding physical locations in three-dimensional space, wherein the obtaining of the imaging scene parameters comprises identifying, based at least in part on a first conic that describes one or more geometries of at least a fixator ring of the plurality of fixator elements, the respective locations of the plurality of fixator elements in the first and the second two-dimensional images; and
    reconstructing, by the one or more computing devices, a three dimensional representation of the first and the second bone segments with respect to the fixation apparatus based upon the imaging scene parameters.

11. The computer-implemented method of claim 10, wherein the identifying is based at least in part on a plurality of conics comprising the first conic and a second conic.

12. The computer-implemented method of claim 11, wherein the second conic describes one or more other geometries of one or more other fixator elements of the plurality of fixator elements.

13. The computer-implemented method of claim 10, wherein the obtaining of the imaging scene parameters is based on a comparison of the respective locations of the plurality of fixator elements in the first and the second two-dimensional images with the corresponding physical locations of the plurality of fixator elements in three-dimensional space.

14. The computer-implemented method of claim 10, wherein the obtaining of the imaging scene parameters further comprises:
    constructing first and second transformation matrices corresponding to the first and second two-dimensional images, respectively, using the respective locations of the plurality of fixator elements; and
    decomposing the first and the second transformation matrices into the imaging scene parameters.

15. The computer-implemented method of claim 14, wherein the constructing of the first and the second transformation matrices is based at least in part on one or more lines representing at least one of the plurality of fixator elements.

16. The computer-implemented method of claim 15, wherein the constructing of the first and the second transformation matrices comprises constructing rows of matrices based on the one or more lines.

17. The computer-implemented method of claim 15, wherein the constructing of the first and the second transformation matrices is based, at least in part, on a point value and a gradient value for each of the one or more lines.

18. The computer-implemented method of claim 10, further comprising identifying respective locations of a plurality of bone elements in the first and the second two-dimensional images, the plurality of bone elements comprising anatomical features of the first and the second bone segments.

19. The computer-implemented method of claim 18, wherein the three dimensional representation is further reconstructed based upon the respective locations of the plurality of bone elements.

20. The computer-implemented method of claim 10, wherein the first and the second orientations are not orthogonal with respect to each other.

* * * * *